United States Patent [19]

Teulon

[11] 4,182,896
[45] Jan. 8, 1980

[54] INDANE DERIVATIVES

[75] Inventor: Jean-Marie Teulon, La Celle Saint-Cloud, France

[73] Assignee: Societe Hexachimie, France

[21] Appl. No.: 788,033

[22] Filed: Apr. 15, 1977

Related U.S. Application Data

[62] Division of Ser. No. 690,391, May 27, 1976, Pat. No. 4,069,326, which is a division of Ser. No. 546,095, Jan. 31, 1975, abandoned.

[30] Foreign Application Priority Data

Feb. 7, 1974 [GB] United Kingdom ............... 5726/74
Aug. 23, 1974 [GB] United Kingdom ............. 37220/74
Dec. 16, 1974 [GB] United Kingdom ............. 54292/74

[51] Int. Cl.² ............... C07C 69/76; A61K 31/235
[52] U.S. Cl. ........................................ 560/8; 424/308
[58] Field of Search ............................................ 560/8

[56] References Cited

U.S. PATENT DOCUMENTS

| | | | |
|---|---|---|---|
| 3,264,308 | 8/1966 | van der Stelt | 560/8 |
| 3,452,085 | 6/1969 | Lauria et al. | 260/515 R |
| 3,668,251 | 6/1972 | Hamilton | 560/8 |
| 3,812,180 | 5/1974 | Shen et al. | 560/8 |
| 3,954,852 | 5/1976 | Shen et al. | 560/8 |

OTHER PUBLICATIONS

Arnold, "Chem. Absts.", vol. 38, 966(6), 1944.

*Primary Examiner*—James O. Thomas, Jr.
*Assistant Examiner*—G. T. Breitenstein
*Attorney, Agent, or Firm*—Bacon & Thomas

[57] ABSTRACT

The present invention relates to certain indane derivatives of general formula

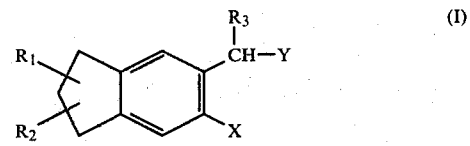

in which: X represents a hydrogen or halogen atom; $R_1$ and $R_2$, which may be identical or different, each represents a hydrogen atom, an alkyl group containing 1 to 5 carbon atoms or a cycloalkyl group containing 3 to 7 carbon atoms; $R_3$ represents a hydrogen atom or an alkyl group containing 1 to 5 carbon atoms; and Y represents —CH₂OH or a group of formula —COOR₄ in which $R_4$ represents a hydrogen atom, 1/v(M) where M is a metal of valency v, or a group of formula

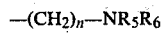

wherein n is an integer of 1 to 5 and $R_5$ and $R_6$, which may be identical or different, each represents an alkyl group containing 1 to 5 carbon atoms, a cycloalkyl group containing 3 to 7 carbon atoms, an aryl group or an aralkyl group, or $R_5$ and $R_6$, together with the nitrogen atom to which they are bonded, form an N-heterocyclic group with 5 to 7 ring members, which heterocyclic group optionally contains a second hetero-atom, and their pharmaceutically acceptable addition salts, and to processes for their preparation. The compounds of formula (I) and their salts are useful for the treatment of inflammations, algias, rheumatisms or pain syndromes in animals.

4 Claims, No Drawings

INDANE DERIVATIVES

This is a division of application Ser. No. 690,391, filed May 27, 1976, now U.S. Pat. No. 4,069,326, which is in turn a division of application Ser. No. 546,095, filed Jan. 31, 1975, now abandoned.

The present invention relates to certain indane derivatives, to processes for their preparation and to their use in therapy.

The present invention provides a compound of general formula:

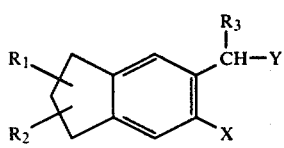

in which: X represents a hydrogen or halogen atom; $R_1$ and $R_2$, which may be identical or different, each represents a hydrogen atom an alkyl group containing 1 to 5 carbon atoms or a cycloalkyl group containing 3 to 7 carbon atoms; $R_3$ represents a hydrogen atom or an alkyl group containing 1 to 5 carbon atoms; and Y represents —$CH_2OH$ or a group of formula —$COOR_4$ in which $R_4$ represents a hydrogen atom, 1/v (M) where M is a metal of valency, v, or a group of formula:

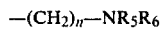

—$(CH_2)_n$—$NR_5R_6$ wherein n is an integer of 1 to 5 and $R_5$ and $R_6$, which may be identical or different, each represents an alkyl group containing 1 to 5 carbon atoms, a cycloalkyl group containing 3 to 7 carbon atoms, an aryl group or an aralkyl group, or $R_5$ and $R_6$, together with the nitrogen atom to which they are bonded, form an N-heterocyclic group with 5 to 7 ring members, which heterocyclic group optionally contains a second heteroatom (e.g. a nitrogen, oxygen or sulfur atom) and/or one or more substituents (e.g. alkyl groups containing 1 to 5 carbon atoms), or a pharmaceutically acceptable addition salt of a compound of formula (I).

The aforesaid alkyl groups of 1 to 5 carbon atoms may be straight or branched; similarly, the group —$(CH_2)_n$ may be straight or branched. The cycloalkyl groups of 3 to 7 carbon atoms may be, for example, cyclopropyl, cyclobutyl, cyclopentyl, cyclohexyl, or cycloheptyl, cyclohexyl being preferred. The substituents $R_1$ and $R_2$ may be on the same or different carbon atoms of the indane nucleus.

The metal M is preferably from group I, II or III of the periodic classification; sodium, potassium, calcium and aluminium are especially suitable.

Suitable N-heterocyclic groups —$NR_5R_6$ include, more especially, pyrrolidino, morpholino, thiomorpholino, 3,5-dimethyl-morpholino, piperidino, 4'-methyl-piperidino, piperazino, 4-(β-hydroxyethyl)-piperazino, 4-p-chlorophenylpiperazino and azepino.

When $R_4$ is an aryl group, it may be, for example, phenyl, and when it is aralkyl, it may be, e.g. α-phenylethyl, β-phenylethyl, or benzyl.

The invention includes the addition salts of the compounds of the formula I, especially the addition salts with amines when $R_4$ is hydrogen and the addition salts with acids or quaternary ammonium salts when $R_4$ is —$(CH_2)_nNR_5R_6$. The addition salts with acids may be produced by reaction of the base with an inorganic or organic acid in manner known per se. Suitable acids for this purpose are, more especially, hydrochloric, sulphuric, phosphoric, oxalic, succinic, methanesulphonic, cyclohexylsulphamic, formic, aspartic, glutamic, N-acetyl-aspartic, N-acetyl-glutamic, ascorbic, maleic, malic, fumaric, lactic, benzoic, cinnamic and p-toluenesulphonic acids.

Particularly preferred compounds of formula (I) are those in which $R_1$ and $R_2$ each represents a hydrogen atom or a methyl, ethyl, isopropyl or cyclohexyl group, $R_3$ represents a hydrogen atom or a methyl or ethyl group and X represents a hydrogen atom. If Y represents a group of formula —$COOR_4$, $R_4$ preferably a hydrogen atom or a group of formula

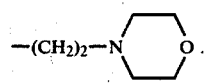

The compounds of formula (I) can be prepared by conventional techniques. In many cases an indane of the formula:

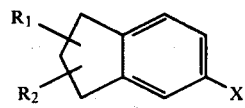

in which $R_1$, $R_2$ and X are as hereinbefore defined, is a convenient starting material. Typical processes which can be used are the following:

(A) A process which comprises:
(a) reacting a compound of the formula

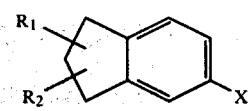

in which $R_1$, $R_2$ and X are as hereinbefore defined with an ethyloxalyl halide and hydrolysing the resulting keto-ester of formula:

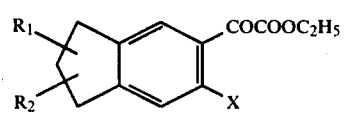

under acidic or basic conditions to obtain a keto-acid of the formula:

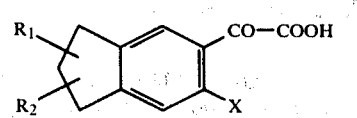

and either:
(b) subjecting the keto-acid of formula (VI) to a Wolff-Kishner reduction to obtain a compound of formula (I) in which Y represents a —COOH group and $R_3$ represents a hydrogen atom, or
(c) reacting the keto-acid of formula (VI) with an organo-magnesium compound of the formula $R_3MgZ$ in which Z is a halogen atom and $R_3$ is an alkyl group containing 1 to 5 carbon atoms to obtain a compound of formula:

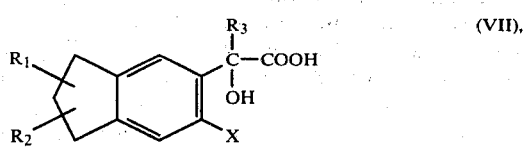

dehydrating the compound of formula (VII) to obtain a compound of formula:

in which R'$_3$ represents a group of formula —(CH$_2$)$_{x-1}$H where x is the number of carbon atoms in R$_3$, and hydrogenating the compound of formula (VIII) to obtain a compound of formula (I) in which Y represents a —COOH group and R$_3$ represents an alkyl group containing 1 to 5 carbon atoms; and if desired, converting the compound of formula (I) obtained in step (b) or (c) into a pharmaceutically acceptable addition salt thereof.

The preferred ethyloxalyl halide for use in step (a) is the chloride and the preferred compounds of formula R$_3$MgZ for use in step (c) are those in which Z is iodine.

The various steps of process A may be carried out using methods known in the art; for example step (a) may be carried out under typical Friedel-Crafts' reaction conditions in the presence of a Lewis acid such as AlCl$_3$ and a solvent such as ethylene chloride and step (b) may be carried out using hydrazine in a solution containing sodium or potassium ions. The Grignard reaction in step (c) is suitably carried out in an ether solvent, the dehydration of the compound of formula VII may be carried out using a strong acid such as concentrated sulphuric acid and the final hydrogenation is suitably carried out in the presence of a catalyst, for example Raney nickel.

Process (A) is illustrated by the following reaction scheme:

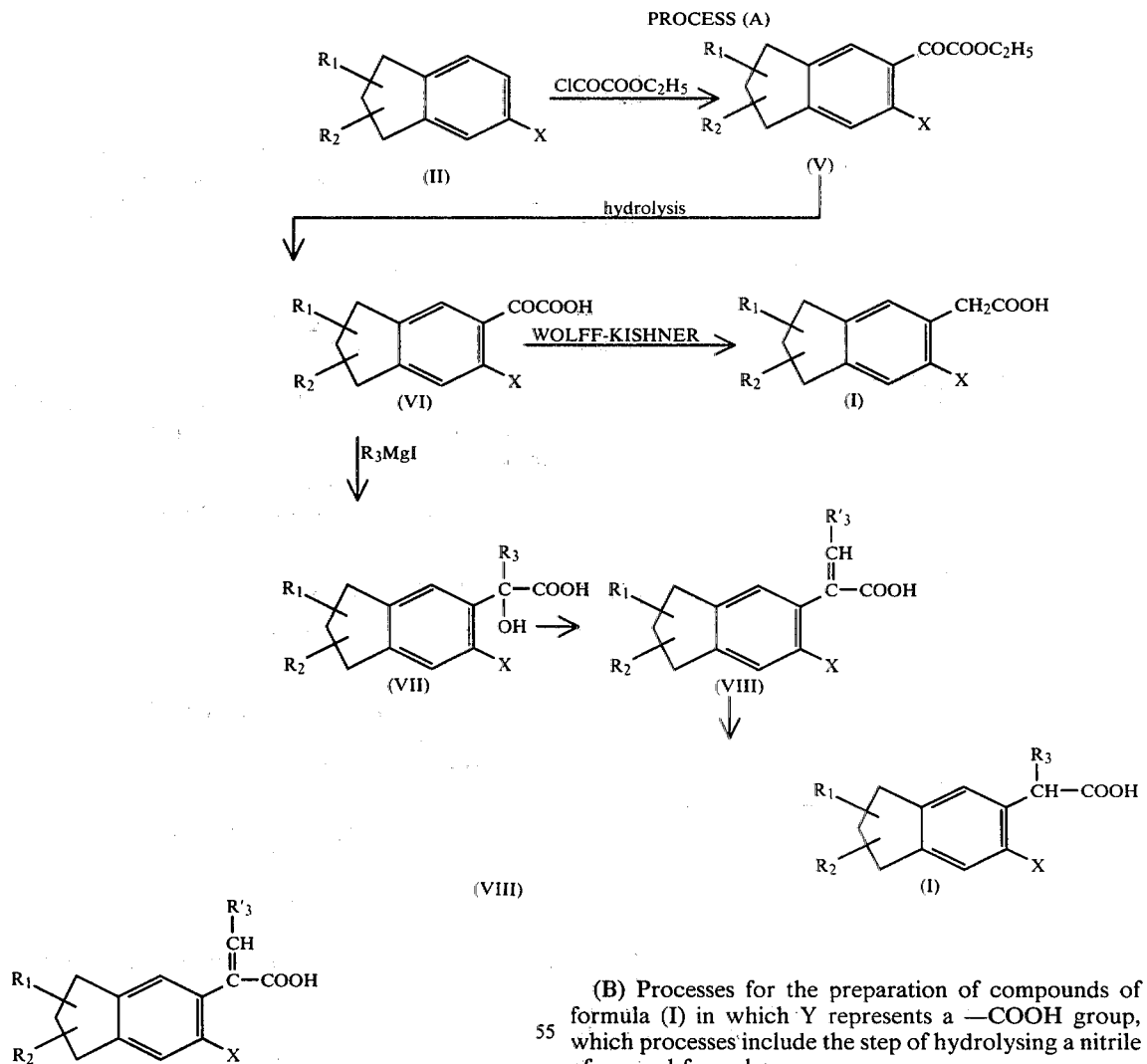

(B) Processes for the preparation of compounds of formula (I) in which Y represents a —COOH group, which processes include the step of hydrolysing a nitrile of general formula:

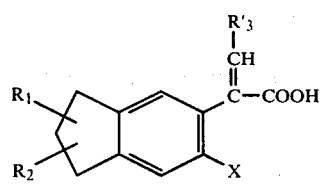

in which R$_1$, R$_2$, R$_3$ and X are as hereinbefore defined under acidic or basic conditions, and, if desired, converting the resulting compound of formula (I) into a pharmaceutically acceptable addition salt thereof.

A nitrile of the formula (IVa) in which $R_3$ represents an alkyl group containing 1 to 5 carbon atoms can be obtained by reacting a nitrile of formula (IVa) in which $R_3$ represents a hydrogen atom with a metallating agent such as sodium or potassium hydride or amide or potassium tert-butylate and reacting the resulting compound of formula:

(XII) [structure: indane with $R_1$, $R_2$ substituents; aromatic ring bearing CHM—CN and X]

in which M is an alkali metal atom, with a halide of formula $R_3Z$ in which $R_3$ represents an alkyl group containing 1 to 5 carbon atoms and Z is a halogen atom, preferably bromine or iodine.

Further processes of general type (B) are the following processes (C) and (D).

(C) A process which comprises (a) chloromethylating in known manner a compound of the formula:

(II) [structure: indane with $R_1$, $R_2$ and X]

in which $R_1$, $R_2$ and X are as hereinbefore defined to obtain a compound of formula:

(III) [structure: indane with $R_1$, $R_2$, CH$_2$Cl and X]

(b) reacting the compound of formula (III) with an alkali metal cyanide to obtain a compound of formula:

(IV) [structure: indane with $R_1$, $R_2$, CH$_2$CN and X]

and (c) hydrolysing the compound of formula (IV) under acidic or basic conditions to obtain a compound of formula (I) in which Y represents a —COOH group and $R_3$ represents a hydrogen atom, and, if desired, converting the compound of formula (I) into a pharmaceutically acceptable addition salt thereof.

Step (a) is preferably carried out using hydrochloric acid and formaldehyde or trioxymethylene.

Process (C) is illustrated by the following reaction scheme:

PROCESS (C)

[structure (II)] $\xrightarrow{\text{CH}_2\text{O} / \text{HCl}}$

-continued
PROCESS (C)

[structure (III): $R_1$, $R_2$-indane with CH$_2$Cl and X] $\xrightarrow{\text{MCN}}$

[structure (IV): $R_1$, $R_2$-indane with CH$_2$CN and X] $\longrightarrow$

[structure (I): $R_1$, $R_2$-indane with CH$_2$COOH and X]

(D) A process which comprises
(a) reacting a compound of the formula:

(IIa) [structure: indane with $R_1$, $R_2$]

in which $R_1$ and $R_2$ are as defined in claim 1 in known manner with a halide or anhydride of an acid of formula $R_3$—COOH in which $R_3$ represents an alkyl group containing 1 to 5 carbon atoms, to obtain a ketone of formula:

(XIII) [structure: $R_1$, $R_2$-indane with CO—$R_3$ substituent]

in which $R_1$, $R_2$ and $R_3$ are as hereinbefore defined.

(b) reducing the ketone of formula (XIII) in known manner to obtain an alcohol of formula:

(XIV) [structure: $R_1$, $R_2$-indane with CHOH—$R_3$]

(c) converting the alcohol of formula (XIV) in known manner into a halide of formula:

(XV) [structure: $R_1$, $R_2$-indane with CHQ—$R_3$]

in which Q is chlorine or bromine.

(d) reacting the halide of formula (XV) with an alkali metal cyanide to obtain a compound of formula:

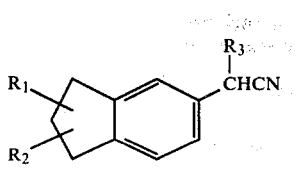
(IVa)

and (e) hydrolysing the compound of formula (IVa) under acidic or basic conditions to obtain a compound of formula (I) in which X represents a hydrogen atom, $R_3$ represents an alkyl group containing 1 to 5 carbon atoms and Y represents a —COOH group, and if desired, converting the compound of formula (I) into a pharmaceutically acceptable addition salt thereof.

The various steps of process (D) may be carried out using method known in the art; step (a) may be carried out under typical Friedel-Crafts' reaction conditions, step (b) may be carried out using conventional reducing agents suitable for reducing a ketone to an alcohol, for example an alkali metal borohydride or lithium aluminum hydride, and step (c) may be carried out using, for example, phosphorus tribromide or thionyl chloride.

Process (D) is illustrated by the following reaction scheme:

PROCESS (D)

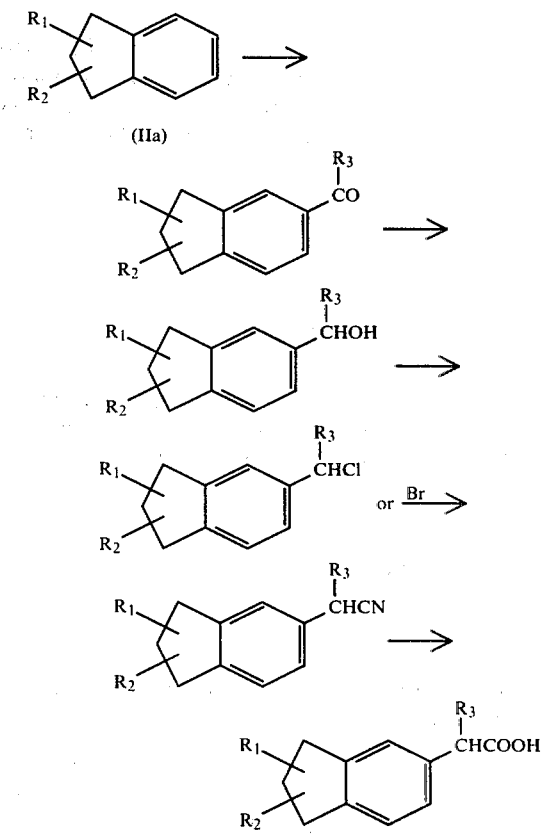

Another process which may be used to prepare compounds of formula (I) in which $R_3$ represents a hydrogen atom and Y represents a —COOH group is the following:

(E) A process which comprises reacting a compound of the formula:

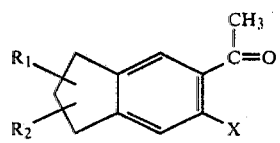
(X)

in which $R_1$, $R_2$ and X are as hereinbefore defined in known manner with sulphur and a primary or secondary amine of formula $NHR_5R_6$ wherein $R_5$ and $R_6$ are as hereinbefore defined with the proviso that at least one of $r_5$ and $R_6$ is other than hydrogen, to obtain a thioamide of the formula:

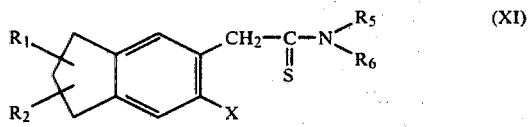
(XI)

in which $R_1$, $R_2$, $R_5$, $R_6$ and X are as hereinbefore defined, and hydrolysing the thioamide of formula (XI) to obtain a compound of formula (I) in which $R_3$ represents a hydrogen atom and Y represents a —COOH group, and, if desired, converting the compound of formula (I) into a pharmaceutically acceptable addition salt thereof.

This process involves a Willgerodt reaction (a variation of the Kindler reaction). The ketones of formula (X) in which X represents a hydrogen atom can be obtained by step (a) of process (D). The hydrolysis of the thioamide is preferably carried out under acid conditions.

The compounds of formula (I) in which Y represents a —CH$_2$OH group can be prepared by methods including the step of reducing a compound of formula:

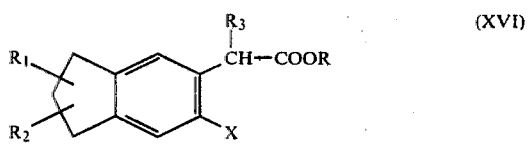
(XVI)

in which $R_1$, $R_2$, $R_3$ and X are as hereinbefore defined and R represents a hydrogen atom or an alkyl group containing 1 to 4 carbon atoms. The compounds of formula (XVI) in which R is hydrogen can be prepared by any of the processes (A) to (E) described above and the compounds in which R is an alkyl group can be obtained by conventional esterification of the corresponding acid. The reduction can be carried out by means of a reducing agent, for example, lithium aluminium hydride, in an organic solvent such as ether or tetrahydrofuran.

The compounds of formula (I) in which Y represents a group of formula —COOR$_4$ in which R$_4$ represents a group of formula —(CH$_2$)$_n$—NR$_5$R$_6$ can be prepared by a process of the following type:

(F) A process which comprises either (a) reacting the halide of an acid of formula:

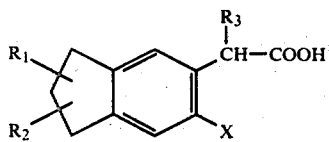

in which $R_1$, $R_2$, $R_3$ and $X$ are as hereinbefore defined with an aminoalcohol of the formula:

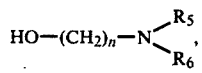

in which n, $R_5$ and $R_6$ are as hereinbefore defined or (b) reacting a salt of an acid of formula (Ia) with a halide of the formula:

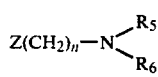

in which n, $R_5$ and $R_6$ are as hereinbefore defined and Z is a halogen atom.

Process (F) is illustrated by the following reaction scheme:

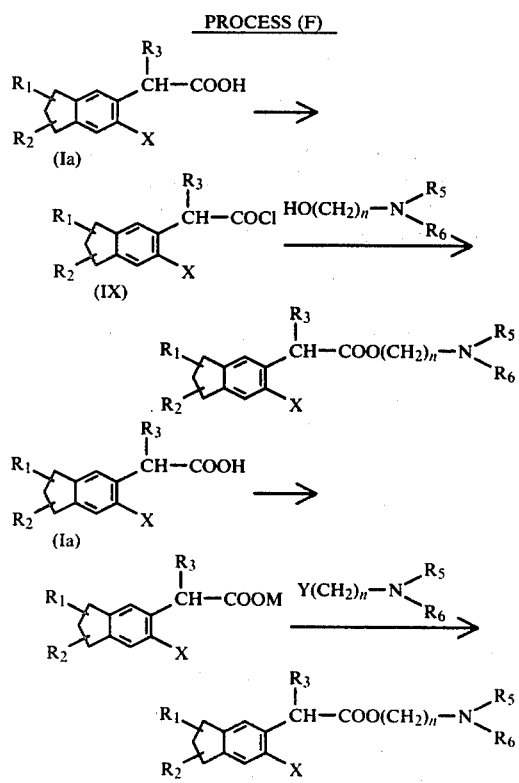

The compounds of the invention and their nontoxic addition salts possess valuable pharmacological activities and are useful in therapy, especially as analgesic and anti-inflammatory agents. They can, for example, be used as anti-inflammatory agents for counteracting rheumatism.

The invention therefore also provides therapeutic compositions which are especially useful in the treatment of inflammations and algias, rheumatisms and pain syndromes which compositions comprise a pharmaceutically effective amount of at least one compound of formula (I) or one of its non-toxic addition salts and a pharmaceutically acceptable carrier or diluent.

The compounds of formula (I) can, for example, be administered to man in the form of gelatine-coated pills containing 50 to 250 mg of active principle at a dose of 2 to 6 gelatine-coated pills per day, in the form of suppositories containing 100 to 500 mg of active principle at a daily dose of 2 to 5 suppositories per day, in the form of a potable suspension containing 25 mg of active principle per 5 cm$^3$ at a daily dose of 10 to 40 cm$^3$ or in the form of an injectable solution containing 50 mg of active principle per 2 ml of solution at a daily dose of 2 to 4 injections.

The compounds of formula (I) possess an LD50 in rate of approximately 250 mg/kg when administered orally, have little tendency to cause ulcers, and possess an activity to toxicity ratio which is generally higher than that of the known products possessing similar pharmacological properties.

The invention is illustrated by the following Examples. Examples 2 to 7 and 11 to 18 illustrate process (A), Example 1 illustrates process (C), Example 26 illustrates process (D), Example 36 illustrates process (E) and Examples 8,9 and 21 to 32 illustrate process (F). Examples 33 to 35 and 37 illustrate the preparation of compounds in which Y is —CH$_2$OH and Examples 19 and 20 illustrate the preparation of addition salts.

EXAMPLE 1

[1,3-Dimethyl-indanyl-(5)]-acetic acid (a) 1,3-Dimethyl-5-chloromethyl-indane

Formula III
$R_1=R_2=CH_3$
$X=H$

A mixture of 73 g of 1,3-dimethyl-indane, 28 g of trioxymethylene, 64 L ml of acetic acid, 41 ml of 85% strength phosphoric acid and 100 ml of concentrated hydrochloric acid is stirred for 24 hours at between 58° and 60° C. The reaction mixture is taken up in a mixture of water and ice and the organic products are extracted with ether. The ether phase is washed with water and dried over sodium sulphate. After evaporation of the ether, the residue obtained is distilled in vacuo. 44.8 g of 1,3-dimethyl-5-chloromethylindane are thus obtained in the form of a colourless liquid.

Boiling point$_{1 \, mm \, Hg}$=110° C.

(b) [1,3-Dimethyl-indanyl-(5)]-acetonitrile

Formula IV
$R_1=R_2=CH_3$
$X=H$

A solution of 25 g of potassium cyanide in 30 ml of water is added over the course of 1 hour to a solution of 44.8 g of 1,3-dimethyl-5-chloromethyl-indane in 130 ml of ethanol. The reaction mixture is heated under reflux for 4 hours and is then cooled, diluted with a mixture of water and ice and extracted with ether. The ether phase is washed carefully with water and dried over sodium sulphate. After evaporation of the ether, the residue obtained is distilled in vacuo. 31.8 g of [1,3-dimethyl-indanyl-(5)]-acetonitrile are thus obtained in the form of a colourless liquid.

Boiling point$_{0.7 \, mm \, Hg}$=125°–132° C.

(c) [1,3-Dimethyl-indanyl-(5)]-acetic acid

Formula I
$r_1=R_2=CH_3$
$R_3=R_4=X=H$

A solution of 31.8 g of [1,3-dimethyl-indanyl-(5)]-acetonitrile in 175 ml of ethanol containing a solution of 62 g of potassium hydroxide in 100 ml of water is heated under reflux for 16 hours.

After evaporation of the ethanol in vacuo, the reaction mixture is diluted with 200 ml of water and then filtered. The filtrate is acidified at 0° by means of 10% strength hydrochloric acid and the precipitate formed is filtered off, washed with water and dried. After recrystallisation from toluene, 20 g of [1,3-dimethyl-indanyl-(5)]-acetic acid are obtained in the form of white crystals.

Melting point = 116°–117° C.

EXAMPLE 2

[1,3-Dimethyl-indanyl-(5)]-acetic acid (a) Ethyl [1,3-dimethyl-indanyl-(5)]-glyoxylate Formula V
$R_1=R_2=CH_3$
$X=H$ A solution of 78 g of 1,3-dimethyl-indane and 83.5 g of ethyloxalyl chloride in 300 ml of methylene chloride is added, over the course of 1 hour, to a stirred suspension of 125 g of aluminium chloride in 300 ml of methylene chloride, whilst cooling in such a way that the temperature of the reaction mixture remains below 5°. The mixture is then stirred for 2 hours at the temperature of the laboratory and is then poured onto 2 kg of ice and acidified to pH 3 by means of hydrochloric acid. The methylene chloride phase is isolated and the mother liquors are extracted with methylene chloride.

The methylene chloride phases are combined, washed with water saturated with sodium chloride and dried over sodium sulphate. After evaporation of the solvent, 119 g of ethyl [1,3-dimethyl-indanyl-(5)]-glyoxylate are obtained in the form of an oil which is used in crude form for the remainder of the operations.

(b) [1.3-Dimethyl-indanyl-(5)]-glyoxylic acid

Formula VI
$R_1=R_2=CH_3$
$X=H$

A solution of 119 g of ethyl [1,3-dimethyl-indanyl-(5)]-glyoxylate in 600 ml of ethanol is treated with a solution of 20.5 g of sodium hydroxide in 600 ml of water and is heated under reflux for 2 hours. The mixture is then cooled, diluted with 300 ml of water and acidified at 0° by means of 10% strength hydrochloric acid. The mixture is extracted with chloroform which is then washed with water saturated with sodium chloride, dried over sodium sulphate and evaporated. After vacuum distillation of the residue obtained, 77 g of [1,3-dimethyl-indanyl -(5)]-glyoxylic acid are isolated.

Boiling point$_{1.5\ mm\ Hg}$ = 170° C.

(c) [1,3-Dimethyl-indanyl-(5)]-acetic acid

Formula I
$R_1=R_2=CH_3$
$R_3=R_4=X=H$

A mixture of 12 g of [1,3-dimethyl-indanyl-(5)]-glyoxylic acid and 25 ml of hydrazine hydrate is heated under reflux for 30 minutes. The mixture is cooled to 70° C. and 15 g of potassium hydroxide pellets are added in small portions.

After the end of the addition, the mixture is heated under reflux for 1 hour 30 minutes and then the excess hydrazine hydrate is evaporated in vacuo. The solution is then cooled and acidified at 0° C. by means of 10% strength hydrochloric acid. The precipitate obtained is filtered off, washed with water and dried. After recrystallisation from toluene, 7.7 g of [1,3-dimethyl-indanyl-(5)]-acetic acid are obtained in the form of white crystals.

Melting point 116°–117° C.

EXAMPLE 3

[6-Chloro-1,3-dimethyl-indanyl-(5)]-acetic acid (a) Ethyl [6-chloro-1,3-dimethyl-indanyl-(5)]-glyoxylate Formula V
$R_1=R_2=CH_3$
$X=Cl$ Following the procedure of Example 2(a) but using 50 g of 1,3-dimethyl-6-chloro-indane and 43 g of ethyloxalyl chloride, 80 g of ethyl [6-chloro-1,3-dimethyl-indanyl-(5)]-glyoxylate are obtained in the form of an oil which is used in crude form for the remainder of the operations.

(b) [6-Chloro-1,3-dimethyl-indanyl-(5)]-glyoxylic acid

Formula VI
$R_1=R_2=CH_3$
$X=Cl$

Following the procedure of Example 2(b) but starting from 80 g of ethyl [6chloro-1,3-dimethyl-indanyl-(5)]-glyoxylate, 61 g of [6-chloro-1,3-dimethyl-indanyl-(5)]-glyoxylic acid are obtained in the form of pale yellow crystals.

Melting point 170°–173° C.

(c) [6-Chloro-1,3-dimethyl-indanyl-(5)]-acetic acid

Formula I
$R_1=R_2=CH_3$
$X=Cl$
$R_3=R_4=H$

Following the procedure of Example 2(c) but starting from 20 g of [6-chloro-1,3-dimethyl-indanyl-(5)]-glyoxylic acid, 10.5 g of [6-chloro-1,3-dimethyl-indanyl-(5)]-acetic acid are obtained in the form of white crystals, after recrystallisation from toluene.

Melting point 158°–160° C.

EXAMPLE 4

[2-Isopropyl-indanyl-(5)]-acetic acid (a) Ethyl [2-isopropyl-indanyl-(5)]-glyoxylate Formula V
$R_1=X=H$
$R_2=$ isopropyl Following the procedure of Example 2(a) but using 43 g of 2-isopropyl-indane and 42.2 g of ethyloxalyl chloride, 69 g of ethyl [2-isopropyl-indanyl-(5)]-glyoxylate are obtained in the form of an oil which is used in crude form for the remainder of the operations.

(b) 2-[2-Isopropyl-indanyl-(5)]-glyoxylic acid

Formula VI $R_1=X=H$
$R_2=$ isopropyl

Following the procedure of Example 2(b) but starting from 69 g of ethyl [2-isopropyl-indanyl-(5)]-glyoxylate, 58 g of 2-[2-isopropyl-indanyl-(5)]-glyoxylic acid are obtained in the form of pale yellow crystals, recrystallised from a 50/50 mixture of hexane and cyclohexane.

Melting point 55°–60° C.

(c) [2-Isopropyl-indanyl-(5)]-acetic acid

Formula I
$R_1=X=R_3=R_4=H$
$R_2=$ isopropyl

Following the procedure of Example 2(c) but starting from 20 g of [2-isopropyl-indanyl-(5)]glyoxylic acid, 11 g of [2-isopropyl-indanyl-(5)]-acetic acid are obtained in the form of white crystals, after recrystallisation from hexane.

Melting point 80°–81° C.

EXAMPLE 5

[1-Cyclohexyl-indanyl-(5)]-acetic acid (a) Ethyl [1-cyclohexyl-indanyl-(5)]-glyoxylate Formula V
$R_2=X=H$
$R_1=$ cyclohexyl Following the procedure of Example 2(a) but using 70 g of 1-cyclohexyl-indane and 54.6 g of ethyloxalyl chloride, 110 g of ethyl [1-cyclohexyl-indanyl-(5)]-glyoxylate are obtained in the form of an oil which is used in crude form for the remainder of the operations.

(b) [1-Cyclohexyl-indanyl-(5)]-glyoxylic acid

Formula VI
$R_2=X=H$
$R_1=$ cyclohexyl

Following the procedure of Example 2(b) but starting from 110 g of ethyl [1-cyclohexyl-indanyl-(5)]-glyoxylate, 90 g of [1-cyclohexyl-indanyl-(5)]-glyoxylic acid are obtained in the form of an oil which is used in crude form for the remainder of the operations.

(c) [1-Cyclohexyl-indanyl-(5)]-acetic acid

Formula I
$R_2=X=R_3=R_4=H$
$R_1=$ cyclohexyl

Following the procedure of Example 2(c) but starting from 30 g of [1-cyclohexyl-indanyl-(5)]-glyoxylic acid, 15.9 g of [1-cyclohexyl-indanyl-(5)]-acetic acid are obtained in the form of white crystals, after recrystallisation from pentane.

Melting point 75°–78° C.

EXAMPLE 6

Sodium salt of 2-methyl-[1,3-dimethyl-indanyl-(5)]-acetic acid (a) 2-Hydroxy-2-methyl-[1,3-dimethyl-indanyl-(5)]-acetic acid Formula VII
$R_1=R_2=CH_3$
$X=H$ The Grignard reagent, prepared from 34.2 g of magnesium in 75 ml of ether and 105 ml of methyl iodide in 200 ml of ether, is added dropwise to a solution, cooled in ice, of 65.5 g of [1,3-dimethyl-indanyl-(5)]-glyoxylic acid in 900 ml of ether. The addition lasts for 1 hour.

The reaction mixture is then stirred at the temperature of the laboratory for 2 hours and is then poured onto 2 kg of ice and acidified by means of 10% strength hydrochloric acid. The mixture is extracted with ethyl acetate and the extract is washed with water and dried. After evaporation of the solvent, 53 g of 2-hydroxy-2-methyl-[1,3-dimethyl-indanyl-(5)]-acetic acid are obtained and are used in crude form for the remainder of the operations.

(b) 2-Methylene-[1,3-dimethyl-indanyl-(5)]-acetic acid

Formula VIII
$R_1=R_2=CH_3$
$X=H$

A solution of 48 g of 2-hydroxy-2-methyl-[1,3-dimethyl-indanyl-(5)]-acetic acid in 2.1 liters of dioxane and 195 ml of concentrated sulphuric acid is heated under reflux for 2 hours and is then cooled and poured onto 2 kg of ice and extracted with chloroform.

The extracts are washed with water and dried over sodium sulphate. After evaporation of the solvent, 42 g of 2-methylene-[1,3-dimethyl-indanyl-(5)]-acetic acid are obtained in the form of light beige crystals.

Melting point 66°–69° C. after recrystallisation from pentane.

(c) Sodium salt of 2-methyl-[1,3-dimethyl-indanyl-(5)]-acetic acid

Formula I
$R_1=R_2=R_3=CH_3$
$X=H$
$R_4=Na$ 35.5 g of 2-methylene-[1,3-dimethyl-indanyl-(5)]-acetic acid dissolved in 350 ml of methanol are hydrogenated in the presence of 10 g of Raney nickel at 80° C. under 40 kg for 7 hours. After cooling, filtration and evaporation of the filtrate, a thick white oil is obtained which does not crystallise. 21.4 g of this oil are treated with a solution of 20 ml of sodium ethylate prepared from 2 g of sodium dissolved in 20 ml of ethanol. After evaporation of the solvent, the residue is taken up in ether and 16 g of the sodium salt of 2-methyl-[1,3-dimethyl-indanyl-(5)]-acetic acid are obtained in the form of a white powder which is soluble in water.

Analysis: potentiometric determination (perchloric acid). Molecular weight found: 239.6. Molecular weight calculated: 240.

EXAMPLE 7

2-Methyl-[2-Isopropyl-indanyl-(5)]-acetic acid (a) 2-Hydroxy-2-methyl-[2-isopropyl-indanyl-(5)]-acetic acid Formula VII
$R_1=X=H$
$R_2=$ isopropyl Following the procedure of Example 6(a) but starting from 44 g of [2-isopropyl-indanyl-(5)]-glyoxylic acid, 39 g of 2-hydroxy-2-methyl-[2-isopropyl-indanyl-(5)]-acetic acid are obtained in the form of white crystals, after recrystallisation from isopropanol.

Melting point 140°–143° C.

(b) 2-Methylene-[2-isopropyl-indanyl-(5)]acetic acid

Formula VIII
$R_1=X=H$ $R_2$=isopropyl

Following the procedure of Example 6(b) but using 21.8 g of 2-hydroxy-2-methyl-[2-isopropyl-indanyl-(5)]-acetic acid, 19 g of 2-methylene-[2-isopropyl-indanyl-(5)]-acetic acid are obtained in the form of light beige crystals.

Melting point 145°–148° C.

(c) 2-Methyl-[2-isopropyl-indanyl-(5)]-acetic acid

Formula I
$R_1$=X=$R_4$=H
$R_2$=isopropyl
$R_3$=CH$_3$

A solution of 19 g of 2-methylene-[2-isopropyl-indanyl-(5)]-acetic acid in 250 ml of dioxane containing 1.5 g of 5% strength Pd/C is hydrogenated under a pressure of 50 kg for 4 hours. The catalyst is filtered off and the filtrate is concentrated in vacuo. 15 g of 2-methyl-[2-isopropyl-indanyl-(5)]-acetic acid are thus obtained in the form of white crystals, after recrystallisation from pentane.

Melting point 81°–83° C.

EXAMPLE 8

Hydrochloride of the morpholino-ethyl ester of [2-isopropyl-indanyl-(5)]-acetic acid (a) [2-Isopropyl-indanyl-(5)]-acetic acid chloride Formula IX
$R_1$=$R_3$=X=H
$R_2$=isopropyl A solution of 9 g of [2-isopropyl-indanyl-(5)]-acetic acid and 6 g of thionyl chloride in 50 ml of benzene is heated at 80° C. for 2 hours. The solvent and the excess thionyl chloride are then evaporated in vacuo. The oil obtained is used in crude form for the remainder of the operations.

(b) Hydrochloride of the morpholino-ethyl ester of [2-isopropyl-indanyl-(5)]-acetic acid Formula I
$R_1$=$R_3$=X=H
$R_2$=isopropyl

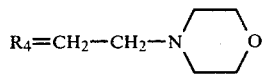

6 g of morpholino-ethanol are added dropwise at 0° C. to a solution of [2-isopropyl-indanyl-(5)]-acetic acid chloride, prepared from 9 g of acid, in 100 ml of ether. The mixture is stirred for 1 hour at ambient temperature and is then taken up in 100 ml of water containing 5% of hydrochloric acid. The aqueous phase is isolated and rendered alkaline at 0° C. by means of a 5% strength solution of sodium hydroxide, and the organic products are extracted with ether. The ether extracts are washed with water and dried over sodium carbonate. After evaporation of the ether, 7 g of the morpholino-ethyl ester of [2-isopropyl-indanyl-(5)]-acetic acid are obtained. On adding a solution of hydrogen chloride in ether and recrystallising from acetone, 7 g of the hydrochloride are obtained in the form of white crystals.

Melting point 153°–156° C.

EXAMPLE 9

Morpholino-ethyl ester of 2-methyl-[2-isopropyl-indanyl-(5)]-acetic acid (a) 2-Methyl-[2-isopropyl-indanyl-(5)]-acetic acid chloride formula IX
$R_1$=X=H
$R_2$=isopropyl
$R_3$=CH$_3$ Following the procedure of Example 8(a), 2-methyl-[2-isopropyl-indanyl-(5)]-acetic acid chloride is prepared from 10 g of acid.

(b) Morpholino-ethyl ester of 2-methyl-[2-isopropyl-indanyl-(5)]-acetic acid

Formula I
$R_1$=X=H
$R_2$=isopropyl
$R_3$=CH$_3$

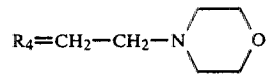

Following the procedure of Example 8(b) but using 2-methyl-[2-isopropyl-indanyl-(5)]-acetic acid chloride prepared from 10 g of acid, 7 g of the morpholino-ethyl ester of 2-methyl-[2-isopropyl-indanyl-(5)]-acetic acid are obtained. After adding 2.55 g of oxalic acid in acetone and recrystallising from acetone, 7.3 g of the oxalate are obtained in the form of white crystals.

Melting point 135°–140° C.

EXAMPLE 10

2-Methyl-[2-isopropyl-indanyl-(5)]-acetic acid (a) [2-Isopropyl-indanyl-(5)]-methyl ketone A solution of 100 g of 2-isopropyl-indane and 65 ml of acetic anhydride in 400 ml of methylene chloride is added over the course of 1 hour to a stirred suspension of 190 g of aluminium chloride in 400 ml of methylene chloride, whilst cooling in such a way that the temperature of the reaction mixture remains below 10° C. The mixture is then stirred for 5 hours at the temperature of the laboratory and is then poured onto 2 kg of ice and acidified to pH 3 by means of hydrochloric acid. The methylene chloride phase is isolated and the mother liquors are extracted with methylene chloride. The methylene chloride phases are combined, washed with water and dried over sodium sulphate. After evaporation of the solvent, the residue, weighing 137 g, is distilled in vacuo; 105.5 g of [2-isopropyl-indanyl-(5)]-methyl ketone are thus obtained in the form of white crystals which melt at a very low temperature (<40° C.).

Boiling point$_{1.5 \ mm \ Hg}$=121°–125° C.

(b) α-[2-Isopropyl-indanyl-(5)]-ethanol 25.6 g of potassium borohydride are added in small portions to a solution of 105.5 g of [2-isopropyl-indanyl-(5)]-methyl ketone in 600 ml of methanol. After the reaction mixture has been stirred magnetically at the temperature of the laboratory for 3 hours, it is concentrated in vacuo, ice is added to it, and the organic products are extracted with ether. After washing with water and drying over sodium sulphate, the ether is evaporated. 106 g of α-[2-isopropyl-indanyl-(5)]-ethanol are thus obtained and are used in crude form for the remainder of the operations.

(c) α-[2-Isopropyl-indanyl-(5)]-ethyl chloride 70 ml of thionyl chloride are added over the course of 2 hours to a solution of 106 g of α-[2-isopropyl-indanyl-(5)]-ethanol in 500 ml of benzene, whilst stirring magnetically. After stirring for 15 minutes at ambient temperature, the reaction mixture is poured onto ice. The benzene phase is isolated and the mother liquors are extracted with ether. The combined organic phases are washed with water, with a 5% strength bicarbonate solution and then again with water and are finally dried over sodium sulphate. After the organic solvents have been evaporated in vacuo, the residue obtained is distilled in vacuo. 104.1 g of α-[2-isopropyl-indanyl-(5)]-ethyl chloride are thus isolated in the form of an oil.

Boiling point$_{1.5\ mm\ Hg}$=132°–136° C.

(d) [2-Isopropyl-indanyl-(5)]-2-methyl-acetonitrile

A solution of 104.1 g of α-[2-isopropyl-indanyl-(5)]-ethyl chloride in 70 ml of dimethylsulphoxide is added dropwise to a solution of 24.3 g of sodium cyanide in 210 ml of dimethylsulphoxide. After the end of the addition, the reaction mixture is heated at 70°–80° C. for 4 hours 30 minutes. The reaction mixture is then cooled, taken up in a mixture of water and ice and extracted with ether. The ether extracts are washed carefully with water and dried over sodium sulphate. After evaporation of the ether, the residue is distilled in vacuo; 74.1 g of [2-isopropyl-indanyl-(5)]-2-methyl-acetonitrile are thus obtained in the form of an oil.

Boiling point$_{1.5\ mm\ Hg}$=135°–150° C.

(e) 2-Methyl-[2-isopropyl-indanyl-(5)]-acetic acid

A solution of 74.1 g of [2-isopropyl-indanyl-(5)]-2-methyl-acetonitrile in 185 ml of ethanol containing 185 ml of water and 74 g of potassium hydroxide is heated under reflux for 12 hours.

Ice and water are added to the reaction mixture and the neutral products are extracted with ether.

After acidifying the cold mother liquors, the acid is extracted with ether. The ether phase is washed with water and dried over sodium sulphate.

After evaporation of the ether and recrystallisation (of the residue) from petroleum ether, 50.6 g of 2-methyl-[2-isopropyl-indanyl-(5)]-acetic acid are obtained in the form of white crystals.

Melting point 81°–83° C.

EXAMPLE 11

[2-Cyclohexyl-indanyl-(5)]-acetic acid (a) Ethyl [2-cyclohexyl-indanyl-(5)]-glyoxylate Formula V
$R_1$=X=H
$R_2$=cyclohexyl A solution of 110.3 g of 2-cyclohexyl-indane and 86 g of ethyloxalyl chloride in 400 ml of methylene chloride is added over the course of 1 hour to a stirred suspension of 128 g of aluminium chloride in 400 ml of methylene chloride, whilst cooling in such a way that the temperature of the reaction mixture remains below 5° C. The mixture is then stirred for 2 hours at the temperature of the laboratory and is then poured onto 2 kg of ice and acidified to pH 3 by means of hydrochloric acid. The methylene chloride phase is isolated and the mother liquors are extracted with methylene chloride. The methylene chloride phases are combined, washed with water saturated with sodium chloride and dried over sodium sulphate.

After evaporation of the solvent, 156.3 g of ethyl [2-cyclohexyl-indanyl-(5)]-glyoxylate are obtained and are used in crude form for the remainder of the operations.

(b) [2-Cyclohexyl-indanyl-(5)]-glyoxylic acid

Formula VI
$R_1$=H
$R_2$=cyclohexyl

A solution of 156.3 g of ethyl [2-cyclohexyl-indanyl-(5)-glyoxylate in 700 ml of ethanol, which has been treated with a solution of 30 g of sodium hydroxide in 700 ml of water, is heated under reflux for 2 hours. The mixture is then cooled, diluted with 350 ml of water and acidified at 0° C. by means of 10% strength hydrochloric acid. The mixture is extracted with ether which is washed with water, dried over sodium sulphate and evaporated. 136 g of [2-cyclohexyl-indanyl-(5)]-glyoxylic acid are thus obtained in the form of pale yellow crystals, after washing with a mixture of pentane and petroleum ether.

Melting point 117°–121° C.

(c) [2-Cyclohexyl-indanyl-(5)]-acetic acid

Formula I
$R_1$=$R_3$=X=H
$R_2$=cyclohexyl

A mixture of 40 g of [2-cyclohexyl-indanyl-(5)]-glyoxylic acid and 100 ml of hydrazine hydrate is heated under reflux for 45 minutes. The mixture is cooled to 70° C. and 50 g of potassium hydroxide pellets are added in small portions. After the end of the addition, the mixture is heated under reflux for 1 hour 30 minutes and then the excess hydrazine hydrate is evaporated in vacuo; the solution is then cooled and diluted with distilled water, and the neutral products are extracted with chloroform.

The mother liquors are acidified at 0° C. by means of 10% strength hydrochloric acid and the acid is extracted with ether which is washed with water, dried and evaporated. After recrystallisation from a 50/50 mixture of cyclohexane and hexane, 29 g of [2-cyclohexyl-indanyl-(5)]-glyoxylic acid are obtained in the form of white crystals.

Melting point 126°–132° C.

EXAMPLE 12

[2-Methyl-indanyl-(5)]-acetic acid (a) Ethyl [2-methyl-indanyl-(5)]-glyoxylate

Formula V
$R_1$=X=H
$R_2$=methyl

Following the procedure of Example 11(a) but using 66 g of 2-methyl-indane and 78.5 g of ethyloxalyl chloride, 110 g of ethyl [2-methyl-indanyl-(5)]-glyoxylate are obtained in the form of an oil which is used in crude form for the remainder of the operations.

(b) [2-Methyl-indanyl-(5)]-glyoxylic acid

Formula VI
$R_1$=X=H
$R_2$=$CH_3$

Following the procedure of Example 11(b) but starting from 110 g of ethyl [2-methyl-indanyl-(5)]-glyoxylate, 98 g of [2-methyl-indanyl-(5)]-glyoxylic acid are obtained and are used in crude form for the remainder of the operations.

(c) [2-Methyl-indanyl-(5)]-acetic acid

Formula I
$R_1=R_3=X=H$
$R_2=CH_3$

Following the procedure of Example 11(c) but starting from 40 g of [2-methyl-indanyl-(5)]-glyoxylic acid, 26 g of [2-methyl-indanyl-(5)]-acetic acid are obtained in the form of white crystals, after recrystallisation from pentane.

Melting point 57°–58° C.

EXAMPLE 13

[2,2-Dimethyl-indanyl-(5)]-acetic acid (a) Ethyl [2,2-dimethyl-indanyl-(5)]-glyoxylate Formula V
$X=H$
$R_1=R_2=CH_3$ Following the procedure of Example 11(a) but using 68 g of 2,2-dimethyl-indane and 73.5 g of ethyloxalyl chloride, 110 g of ethyl [2,2-dimethyl-indanyl-(5)]-glyoxylate are obtained in the form of an oil which is used in crude form for the remainder of the operations.

(b) [2,2-Dimethyl-indanyl-(5)]-glyoxylic acid

Formula VI
$X=H$
$R_1=R_2=CH_3$

Following the procedure of Example 11(b) but starting from 110 g of ethyl [2,2-dimethyl-indanyl-(5)]-glyoxylate, 92 g of [2,2-dimethyl-indanyl-(5)]-glyoxylic acid are obtained and are used in crude form for the remainder of the operations.

(c) [2,2-Dimethyl-indanyl-(5)]-acetic acid

Formula I
$R_3=X=H$
$R_1=R_2=CH_3$

Following the procedure of Example 11(c) but starting from 35 g of [2,2-dimethyl-indanyl-(5)]-glyoxylic acid, 24.7 g of [2,2-dimethyl-indanyl-(5)]-acetic acid are obtained in the form of white crystals, after recrystallisation from pentane.

Melting point <40° C.

EXAMPLE 14

2-Methyl-[2-cyclohexyl-indanyl-(5)]-acetic acid (a) 2-Hydroxy-2-methyl-[2-cyclohexyl-indanyl-(5)]-acetic acid Formula VII
$R_1=X=H$
$R_2=$ cyclohexyl
$R_3=CH_3$ The Grignard reagent prepared from 42.3 g of magnesium and 135 ml of methyl iodide in 850 ml of anhydrous ether is added dropwise to a solution, cooled in ice, of 100 g of [2-cyclohexyl-indanyl-(5)]-glyoxylic acid in 850 ml of anhydrous ether. The addition lasts for 1 hour. The reaction mixture is then stirred at the temperature of the laboratory for 2 hours and is then poured onto kg (sic) of ice and acidified by means of 10% strength hydrochloric acid. The mixture is extracted with ethyl acetate which is washed with water and dried. After evaporation of the solvent and washing the crystals obtained with petroleum ether, 80.2 g of 2-hydroxy-2-methyl-[2-cyclohexyl-indanyl-(5)]-acetic acid are obtained in the form of white crystals.

Melting point 142°–144° C.

(b) 2-Methylene-[2-cyclohexyl-indanyl-(5)]-acetic acid

Formula VIII
$R_1=X=H$
$R_2=$ cyclohexyl
$R'_3=H$

A solution of 80.2 g of 2-hydroxy-2-methyl-[2-cyclohexyl-indanyl-(5)]-acetic acid in 1.950 l of dioxane and 106 ml of concentrated sulphuric acid is heated under reflux for 2 hours and is then cooled and poured onto 2 kg of ice. The precipitate obtained is washed with water and dried. 72 g of 2-methylene-[2-cyclohexyl-indanyl-(5)]-acetic acid are thus obtained in the form of light beige crystals.

Melting point 179°–182° C.

(c) 2-Methyl-[2-cyclohexyl-indanyl-(5)]-acetic acid

Formula I
$R_1=X=H$
$R_2=$ cyclohexyl
$R_3=CH_3$ 72 g of 2-methylene-[2-cyclohexyl-indanyl-(5)]-acetic acid dissolved in 600 ml of dioxane are hydrogenated in the presence of 10 g of Raney nickel at 80° C. under 50 kg for 7 hours. After cooling, filtration and evaporation of the filtrate, the crystals obtained are recrystallised from a 10/90 mixture of toluene and petroleum ether; 48 g of 2-methyl-[2-cyclohexyl-indanyl-(5)]-acetic acid are thus obtained in the form of white crystals.

Melting point 119°–121° C.

EXAMPLE 15

Sodium salt of 2-methyl-[2-methyl-indanyl-(5)]-acetic acid (a) 2-Hydroxy-2-methyl-[2-methyl-indanyl-(5)]-acetic acid Formula VII
$R_1=X=H$
$R_2=R_3=CH_3$ Following the procedure of Example 14(a) but starting from 63 g of [2-methyl-indanyl-(5)]-glyoxylic acid, 48 g of 2-hydroxy-2-methyl-[2-methyl-indanyl-(5)]-acetic acid are obtained in the form of white crystals.

Melting point 97°–100° C.

(b) 2-Methylene-[2-methyl-indanyl-(5)]-acetic acid

Formula VIII
$R_1=X=H$
$R_2=CH_3$
$R'_3=H$

Following the procedure of Example 14(b) but starting from 33 g of 2-hydroxy-2-methyl-[2-methyl-indanyl-(5)]-acetic acid, 29 g of 2-methylene-[2-methyl-indanyl-(5)]-acetic acid are obtained in the form of light beige crystals.

Melting point 119° C.

(c) Sodium salt of 2-methyl-[2-methyl-indanyl-(5)]-acetic acid

Formula I
$R_1=X=H$
$R_2=R_3=CH_3$
$R_4=Na$ 29 g of 2-methylene-[2-methyl-indanyl-(5)]-acetic acid dissolved in 200 ml of methanol are hydrogenated in the presence of 10 g of Raney nickel at 80° C. under 50 kg for 7 hours. After cooling, filtration and evaporation of the filtrate, an oil is obtained which does not crystallise. 14.6 g of this oil are treated with a solution of 20 ml of sodium ethylate prepared from 1.65 g of sodium dissolved in 20 ml of ethanol. After evaporation of the solvent, the residue is taken up in ether and 13 g of the sodium salt of 2-methyl-[2-methyl-indanyl-(5)]-acetic acid are obtained in the form of a white powder which is soluble in water.

Melting point 127°–130° C.

EXAMPLE 16

2-Methyl-[2,2-dimethyl-indanyl-(5)]-acetic acid (a) 2-Hydroxy-2-methyl-[2,2-dimethyl-indanyl-(5)]-acetic acid Formula VII
$X=H$
$R_1=R_2=R_3=CH_3$ Following the procedure of Example 14(a) but starting from 62 g of [2,2-dimethyl-indanyl-(5)]-glyoxylic acid, 37.3 g of 2-hydroxy-2-methyl-[2,2-dimethyl-indanyl-(5)]-acetic acid are obtained in the form of white crystals.

Melting point 99°–103° C.

(b) 2-Methylene-[2,2-dimethyl-indanyl-(5)]-acetic acid

Formula VIII
$X=H$
$R_1=R_2=CH_3$
$R'_3=H$

Following the method of Example 14(b) but starting from 37.3 g of 2-hydroxy-2-methyl-[2,2-dimethyl-indanyl-(5)]-acetic acid, 30.7 g of 2-methylene-[2,2-dimethyl-indanyl-(5)]-acetic acid are obtained in the form of light beige crystals.

Melting point 115° C.

(c) 2-Methyl-[2,2-dimethyl-indanyl-(5)]-acetic acid

Formula I
$X=H$
$R_1=R_2=R_3=CH_3$

Following the procedure of Example 15(c) but starting from 30.7 g of 2-methylene-[2,2-dimethyl-indanyl-(5)]-acetic acid, 22.5 g of 2-methyl-[2,2-dimethyl-indanyl-(5)]-acetic acid are obtained in the form of white crystals, after recrystallisation from pentane.

Melting point 64°–65° C.

EXAMPLE 17

2-Ethyl-[2-isopropyl-indanyl-(5)]-acetic acid (a) 2-Hydroxy-2-ethyl-[2-isopropyl-indanyl-(5)]-acetic acid Formula VII
$R_1=H$
$R_2=isopropyl$
$R_3=C_2H_5$ Following the procedure of Example 14(a) but starting from 64.5 g of [2-isopropyl-indanyl-(5)-glyoxylic acid (described above) and 207 g of ethyl bromide, 70.9 g of 2-hydroxy-2-ethyl-[2-isopropyl-indanyl-(5)]acetic acid are obtained in the form of white crystals.

Melting point 113°–116° C.

(b) 2-Ethylene-[2-isopropyl-indanyl-(5)]-acetic acid

Formula VIII
$R_1=H$
$R_2=isopropyl$
$R'_3=CH_3$

Following the procedure of Example 14(b) but starting from 70.9 g of 2-hydroxy-2-ethyl-[2-isopropyl-indanyl-(5)]-acetic acid, 60.7 g of 2-ethylene-[2-isopropyl-indanyl-(5)]-acetic acid are obtained in the form of light beige crystals.

Melting point 118°–123° C.

(c) 2-Ethyl-[2-isopropyl-indanyl-(5)]-acetic acid

Formula I
$R_1=X=H$
$R_2=isopropyl$
$R_3=C_2H_5$

Following the procedure of Example 15(c) but starting from 60.7 g of 2-ethylene-[2-isopropyl-indanyl-(5)]-acetic acid, 40 g of 2-ethyl-[2-isopropyl-indanyl-(5)]-acetic acid are obtained in the form of white crystals, after recrystallisation from pentane.

Melting point 78°–80° C.

EXAMPLE 18

2-Methyl-[2-ethyl-indanyl-(5)]-acetic acid (a) Ethyl [2-ethyl-indanyl-(5)]-glyoxylate Formula V
$R_1=X=H$
$R_2=C_2H_5$ Following the procedure of Example 11(a) but using 77 g of 2-ethyl-indane and 83 g of ethyloxalyl chloride, 116.3 g of ethyl [2-ethyl-indanyl-(5)]-glyoxylate are obtained in the form of an oil which is used in crude form for the remainder of the operations.

(b) [2-Ethyl-indanyl-(5)]-glyoxylic acid

Formula VI
$R_1=X=H$
$R_2=C_2H_5$

Following the procedure of Example 11(b) but using 116.3 g of ethyl [2-ethyl-indanyl-(5)]-glyoxylate, 93.6 g of [2-ethyl-indanyl-(5)]-glyoxylic acid are obtained and are used in crude form for the remainder of the operations.

(c) 2-Hydroxy-2-methyl-[2-ethyl-indanyl-(5)]-acetic acid

Formula VII
$R_1=X=H$
$R_2=C_2H_5$
$R_3=CH_3$

Following the procedure of Example 14(a) but starting from 93.6 g of [2-ethyl-indanyl-(5)]-glyoxylic acid, 100 g of 2-hydroxy-2-methyl-[2-ethyl-indanyl-(5)]-acetic acid are obtained and are used in crude form for the remainder of the operations.

(b) 2-Methylene-[2-ethyl-indanyl-(5)]-acetic acid

Formula VIII
$R_1=X=H$
$R_2=C_2H_5$
$R'_3=H$

Following the procedure of Example 14(b) but starting from 100 g of 2-hydroxy-2-methyl-[2-ethyl-indanyl-(5)]-acetic acid, 77.5 g of 2-methylene-[2-ethyl-indanyl-(5)]-acetic acid are obtained in the form of crystals.

Melting point 88°–91° C.

(e) 2-Methyl-[2-ethyl-indanyl-(5)]-acetic acid

Formula I
$R_1=X=H$
$R_2=C_2H_5$
$R_3=CH_3$

Following the procedure of Example 15(c) but starting from 77.5 g of 2-methylene-[2-ethyl-indanyl-(5)]-acetic acid, a residue weighing 79 g is obtained and is distilled in vacuo. 53.6 g of 2-methyl-[2-ethyl-indanyl-(5)]-acetic acid are thus isolated and crystallise from pentane in the form of white crystals.

Melting point 44°–46° C.

EXAMPLE 19

Dimethylaminoethanol salt of 2-methyl-[2-isopropyl-indanyl-(5)]-acetic acid

Formula I
$R_1=X=H$
$R_2=$ isopropyl
$R_3=CH_3$ 4.5 g of dimethylaminoethanol are added to 11.6 g of 2-methyl-[2-isopropyl-indanyl-(5)]-acetic acid, melting point 81°–83° C. (described above), dissolved in 50 ml of ether. The solution is concentrated in vacuo and the residue is dilted with 50 ml of pentane. 9.8 g of dimethylaminoethanol salt of 2-methyl-[2-isopropyl-indanyl-(5)]-acetic acid are precipitated under cold conditions in the form of white crystals.

Melting point 59°–60° C.

EXAMPLE 20

Dimethylaminoethanol salt of 2-ethyl-[2-isopropyl-indanyl-(5)]-acetic acid

Formula I
$R_1=X=H$
$R_2=$ isopropyl
$R_3=C_2H_5$

Following the procedure of Example 19 but starting from 13.5 g of 2-ethyl-[2-isopropyl-indanyl-(5)]-acetic acid and 4.9 g of dimethylaminoethanol, 11.2 g of the dimethylaminoethanol salt of 2-ethyl-[2-isopropyl-indanyl-(5)]-acetic acid are obtained in the form of white crystals.

Melting point 69°–71° C.

EXAMPLE 21

Hydrochloride of the morpholino-ethyl ester of [2-methyl-indanyl-(5)]-acetic acid (a) [2-Methyl-indanyl-(5)]-acetic acid chloride Formula IX
$R_1=R_3=X=H$
$R_2=CH_3$ A solution of 11 g of [2-methyl-indanyl-(5)]-acetic acid and 7.5 ml of thionyl chloride in 75 ml of benzene is heated at 80° C. for 2 hours. The solvent and the excess thionyl chloride are then evaporated in vacuo. The residue obtained is fractionated in vacuo to yield 8.6 g of [2-methyl-indanyl-(5)]-acetic acid chloride in the form of a liquid.

Boiling point$_{12\ mm\ Hg}=148°–151°$ C.

(b) Hydrochloride of the morpholino-ethyl ester of [2-methylindanyl-(5)]-acetic acid Formula I
$R_1=R_3=X=H$
$R_2=CH_3$

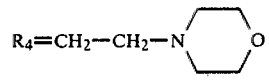

A solution of 8.6 g of [2-methyl-indanyl-(5)]-acetic acid chloride in 50 ml of benzene is added dropwise to a solution of 5.4 g of morpholino-ethanol in 150 ml of anhydrous benzene containing 7.7 ml of triethylmine, whilst keeping the reaction mixture at 0° C. After the end of the addition, the reaction mixture is stirred for 2 hours at ambient temperature and is then left to stand overnight. The benzene phase is isolated and the mother liquors are extracted with ether. The combined organic phases are washed carefully with water and then dried over sodium sulphate. After concentration in vacuo, the residue is taken up in a mixture of acetone and ether and a solution of hydrogen chloride in ether is added thereto to yield 9.4 g of the hydrochloride of the morpholino-ethyl ester of [2-methyl-indanyl-(5)]-acetic acid in the form of white crystals.

Melting point 107°–110° C.

EXAMPLE 22

Oxalate of the morpholino-ethyl ester of 2-methyl-[2-methyl-indanyl-(5)]-acetic acid (a) 2-Methyl-[2-methyl-indanyl-(5)]-acetic acid chloride Formula IX
$R_1=X=H$
$R_2=R_3=CH_3$ A solution of 11.3 g of 2-methyl-[2-methyl-indanyl-(5)]-acetic acid and 7 ml of thionyl chloride in 100 ml of benzene is heated at 80° C. for 2 hours. The solvent and the excess thionyl chloride are then evaporated in vacuo. The oil obtained is used in crude form for the remainder of the operations.

(b) Oxalate for the morpholino-ethyl ester of 2-methyl-[2-methyl-indanyl-(5)]-acetic acid Formula I
$R_1=X=H$
$R_2=R_3=CH_3$

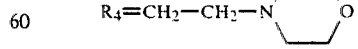

Following the procedure of Example 21(b) but starting from 7g of 2-methyl-[2-methyl-indanyl-(5)]-acetic acid chloride, 6.8 g of the morpholino-ethyl ester of 2-methyl-[2-methyl-indanyl-(5)]-acetic acid are obtained in the form of an oil. On adding 2.7 g of oxalic acid dissolved in ethanol, 7.1 g of the oxalate of the morpholino-ethyl ester of 2-methyl-[2-methyl-indanyl-(5)-]-acetic acid are obtained in the form of white crystals, after recrystallization from isopropanol.

Melting point 140°–145° C.

EXAMPLE 23

Hydrochloride of the morpholino-ethyl ester of [2,2-dimethyl-indanyl-(5)]-acetic acid (a) [2,2-Dimethyl-indanyl-(5)]-acetic acid chloride Formula IX
$R_5=X=H$
$R_1=R_2=CH_3$ Following the procedure of Example 21(a) but starting from 16 g of [2,2-dimethyl-indanyl-(5)]-acetic acid, there are obtained, after distillation of the residue in vacuo, 14.7 g of [2,2-dimethyl-indanyl-(5)]-acetic acid chloride in the form of a liquid.

Boiling point$_{10\ mm\ Hg}$ = 140°–145° C.

(b) Hydrochloride of the morpholino-ethyl ester of [2,2-dimethyl-indanyl-(5)]-acetic acid Formula I
$R_3=X=H$
$R_1=R_2=CH_3$

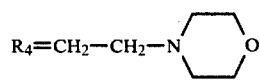

Following the procedure of Example 21(b) but starting from 14.7 g of [2,2-dimethyl-indanyl-(5)]-acetic acid chloride, a residue is obtained after evaporation of the organic solvents in vacuo; this residue is taken up in a mixture of acetone and ether and a solution of hydrogen chloride in ether is added thereto to yield 16 g of the hydrochloride of the morpholino-ethyl ester of [2,2-dimethyl-indanyl-(5)]-acetic acid in the form of white crystals.

Melting point 145°–150° C.

EXAMPLE 24

Hydrochloride of the morpholino-ethyl ester of 2-methyl-[2,2-dimethyl-indanyl-(5)]-acetic acid (a) 2-Methyl-[2,2-dimethyl-indanyl-(5)]-acetic acid chloride Formula IX
$X=H$
$R_1=R_2=R_3=CH_3$ Following the procedure of Example 21(a) but starting from 10.2 g of 2-methyl-[2,2-dimethyl-indanyl-(5)]-acetic acid, 10.5 g of 2-methyl-[2,2-dimethyl-indanyl-(5)]-acetic acid chloride are obtained in the form of an oil which is used in crude form for the remainder of the operations.

(b) Hydrochloride of the morpholino-ethyl ester of 2-methyl-[2,2-dimethyl-indanyl-(5)]-acetic acid Formula I
$X=H$
$R_1=R_2=R_3=CH_3$

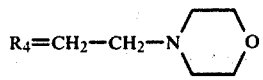

Following the procedure of Example 21(b) but starting from 10.5 g of 2-methyl-[2,2-dimethyl-indanyl-(5)]-acetic acid chloride, there are obtained, after having taken up the residue obtained in a mixture of acetone and ether and after having added a solution of hydrogen chloride in ether thereto, 12 g of the hydrochloride of the morpholino-ethyl ester of 2-methyl-[2,2-dimethyl-indanyl-(5)]-acetic acid in the form of white crystals.

Melting point 140°–142° C.

EXAMPLE 25

Hydrochloride of the morpholino-ethyl ester of 2-methyl-[2-cyclohexyl-indanyl-(5)]-acetic acid (a) 2-Methyl-[2-cyclohexyl-indanyl-(5)]-acetic acid chloride Formula IX
$X=R_2=H$
$R_1=$cyclohexyl
$R_3=CH_3$ Following the procedure of Example 21(a) but starting from 10 g of 2-methyl-[2-cyclohexyl-indanyl-(5)]-acetic acid, 10.2 g of 2-methyl-[2-cyclohexyl-indanyl-(5)]-acetic acid chloride are obtained in the form of an oil which is used in crude form for the remainder of the operations.

(b) Hydrochloride of the morpholino-ethyl ester of 2-methyl-[2-cyclohexyl-indanyl-(5)]-acetic acid Formula I
$X=R_2=H$
$R_1=$cyclohexyl
$R_3=CH_3$

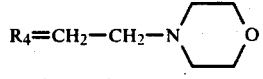

Following the procedure of Example 21(b) but starting from 10.2 g of 2-methyl-[2-cyclohexyl-indanyl-(5)]-acetic acid chloride, there are obtained, after having diluted the residue obtained with a mixture of acetone and ether and after having added a solution of hydrogen chloride in ether thereto, 8.9 g of the hydrochloride of the morpholino-ethyl ester of 2-methyl-[2-cyclohexyl-indanyl-(5)]-acetic acid in the form of white crystals.

Melting point 154°–156° C.

EXAMPLE 26

Oxalate of the morpholino-ethyl ester of 2-methyl-[2-ethyl-indanyl-(5)]-acetic acid (a) 2-Methyl-[2-ethyl-indanyl-(5)]-acetic acid chloride Formula IX
$R_2=X=H$
$R_1=C_2H_5$
$R_3=CH_3$ Following the procedure of Example 21(a) but starting from 19.2 g of 2-methyl-[2-ethyl-indanyl-(5)]-acetic acid, 18.5 g of 2-methyl-[2-ethyl-indanyl-(5)]-acetic acid chloride are obtained, after distillation of the residue in vacuo.

Boiling point$_{10\ mm\ Hg}$=170°–175° C.

(b) Oxalate of the morpholino-ethyl ester of 2-methyl-[2-ethyl-indanyl-(5)]-acetic acid Formula I
R$_2$=X=H
R$_1$=C$_2$H$_5$
R$_3$=CH$_3$

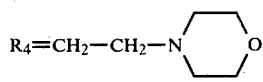

Following the procedure of Example 21(b) but starting from 16.5 g of 2-methyl-[2-ethyl-indanyl-(5)]-acetic acid chloride, 15 g of the morpholino-ethyl ester of 2-methyl-[2-ethyl-indanyl-(5)]-acetic acid are obtained in the form of an oil. On adding 5.5 g of oxalic acid dissolved in ethanol, 15.5 g of the oxalate of the morpholino-ethyl ester of 2-methyl-[2-ethyl-indanyl-(5)]-acetic acid are obtained in the form of white crystals, after recrystallisation from ethanol.

Melting point 143°–145° C.

EXAMPLE 27

Hydrochloride of the dimethylaminoethyl ester of 2-methyl-[2-isopropyl-indanyl-(5)]-acetic acid (a) 2-Methyl-[2-isopropyl-indanyl-(5)]-acetic acid chloride Formula IX
R$_2$=X=H
R$_1$=isopropyl
R$_3$=CH$_3$ Following the procedure of Example 21(a) but using 31.7 g of 2-methyl-[2-isopropyl-indanyl-(5)]-acetic acid, melting point 81°–83° C., described above, there are obtained, after distillation of the residue in vacuo, 30.1 g of 2-methyl-[2-isopropyl-indanyl-(5)]-acetic acid chloride.

Boiling point$_{1\ mm\ Hg}$=150° C.

(b) Hydrochloride of the dimethylaminoethyl ester of 2-methyl-[2-isopropyl-indanyl-(5)]-acetic acid Formula I
R$_1$=X=H
R$_2$=isopropyl
R$_3$=CH$_3$

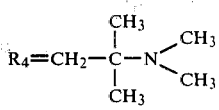

Following the procedure of Example 21(b) but using 10 g of 2-methyl-[2-isopropyl-indanyl-(5)]-acetic acid chloride and 3.6 g of dimethylaminoethanol, a residue is obtained after evaporation of the organic solvents in vacuo; this residue is taken up in a mixture of acetone and ether and a solution of hydrogen chloride in ether is added thereto to yield, after recrystallisation of the crystals obtained from acetone, 11.4 g of the hydrochloride of the dimethylaminoethyl ester of 2-methyl-[2-isopropyl-indanyl-(5)]-acetic acid in the form of white crystals.

Melting point 123°–124° C.

EXAMPLE 28

Oxalate of the diethylaminoethyl ester of 2-methyl-[2-isopropylindanyl-(5)]-acetic acid Formula I
R$_2$=X=H
R$_1$=isopropyl
R$_3$=CH$_3$

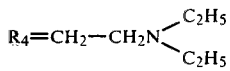

Following the procedure of Example 21(b) but using 10 g of 2-methyl-[2-isopropyl-indanyl-(5)]-acetic acid chloride and 4.1 g of diethylaminoethanol, 10 g of the diethylaminoethyl ester of 2-methyl-[2-isopropyl-indanyl-(5)]-acetic acid are obtained, after evaporation of the organic solvents in vacuo; 3.8 g of oxalic acid dissolved in ethanol are added to the above ester to yield, after recrystallisation from isopropanol, 11 g of the oxalate of the diethylaminoethyl ester of 2-methyl-[2-isopropyl-indanyl-(5)]-acetic acid in the form of white crystals.

Melting point 135°–137° C.

EXAMPLE 29

Maleate of the dimethylamino-α-dimethyl-ethyl ester of 2-methyl-[2-isopropyl-indanyl-(5)]-acetic acid Formula I
R$_2$=X=H
R$_1$=isopropyl
R$_3$=CH$_3$ $$R_4=CH_2-\underset{\underset{CH_3}{|}}{\overset{\overset{CH_3}{|}}{C}}-N\diagdown\!\!\!\diagup\begin{matrix}CH_3\\CH_3\end{matrix}$$

Following the procedure of Example 21(b) but using 10 g of 2-methyl-[2-isopropyl-indanyl-(5)]-acetic acid chloride and 4.1 g of dimethylamino-α-dimethyl-ethanol, 11 g of the dimethylamino-α-dimethyl-ethyl ester of 2-methyl-[2-isopropyl-indanyl-(5)]-acetic acid are obtained; 3.8 g of maleic acid dissolved in acetone are added to the above ester to yield 11.2 g of the maleate of the dimethylamino-α-dimethyl-ethyl ester of 2-methyl-[2-isopropyl-indanyl-(5)]-acetic acid in the form of white crystals.

Melting point 92°–95° C.

EXAMPLE 30

Oxalate of the piperidine-ethyl ester of 2-methyl-[2-isopropyl-indanyl-(5)]-acetic acid Formula I
R$_2$=X=H
R$_1$=isopropyl
R$_3$=CH$_3$

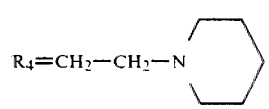

Following the procedure of Example 21(b) but using 14 g of 2-methyl-[2-isopropyl-indanyl-(5)]-acetic acid chloride and 7.2 g of piperidinoethanol, 15 g of ester are obtained; 5.5 g of oxalic acid dissolved in ethanol are added to the above ester to yield 14 g of the oxalate of the piperidinoethyl ester of 2-methyl-[2-isopropyl-indanyl-(5)]-acetic acid in the form of white crystals, after recrystallisation from ethanol.

Melting point 139°–141° C.

EXAMPLE 31

Sodium salt of 2-methyl-[2-isopropyl-indanyl-(5)]-acetic acid

Formula I
$R_2=X=H$
$R_1=$isopropyl
$R_3=CH_3$
$R_4=Na$ 25.5 g of 2-methyl-[2-isopropyl-indanyl-(5)]-acetic acid are treated with a solution of sodium methylate prepared from 2.5 g of sodium dissolved in 40 ml of methanol. After evaporation of the solvent, the residue is taken up in ether and 23 g of the sodium salt of 2-methyl-[2-isopropyl-indanyl-(5)]-acetic acid are obtained in the form of a white powder which is soluble in water.

EXAMPLE 32

Maleate of the pyrrolidino-ethyl ester of 2-methyl-[2-isopropyl-indanyl-(5)]-acetic acid Formula I
$R_2=X=H$
$R_1=$isopropyl
$R_3=CH_3$

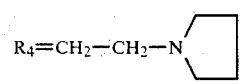

A solution of 11 g of the sodium salt of 2-methyl-[2-isopropyl-indanyl-(5)]-acetic acid and 6.9 of β-chloroethylpyrrolidine in 100 ml of xylene is heated under reflux for 7 hours. After cooling the reaction mixture, the organic phase is washed with water and dried over sodium carbonate. After evaporation of the solvent, a residue weighing 14.3 g is obtained to which a solution of 5 g of maleic acid in acetone is added. 17.4 g of the maleate of the pyrrolidino-ethyl ester of 2-methyl-[2-isopropyl-indanyl-(5)]-acetic acid are thus obtained in the form of white crystals.

Melting point 114°–116° C.

EXAMPLE 33

2-Methyl-β-[2-isopropyl-indanyl-(5)]-ethanol

Formula I
$R_1=H$
$R_2=$isopropyl
$R_3=CH_3$

A solution of 10 g of 2-methyl-[2-isopropyl-indanyl-(5)]-acetic acid in 50 ml of anhydrous ether is added dropwise to a suspension of 3.3 g of lithium aluminum hydride in 50 ml of anhydrous ether. After the end of the addition, the reaction mixture is heated under reflux for 3 hours.

After cooling, a saturated aqueous solution of sodium sulphate is added dropwise at 0° C. in order to destroy the excess hydride. As soon as the hydride no longer reacts, sodium sulphate is added to the reaction and filtration is effected. The precipitate is washed carefully with ether the filtrates are combined and the ether is evaporated. 9.5 g of 2-methyl-β-[2-isoproyl-indanyl-(5)]-ethanol are thus obtained in the form of white crystals.

Melting point 45° C.

EXAMPLE 34

2-Methyl-β-[2-ethyl-indanyl-(5)]-ethanol

Formula I
$R_1=H$
$R_2=C_2H_5$
$R_3=CH_3$

Following the procedure of Example 33 but using 12.8 g of 2-methyl-[2-ethyl-indanyl-(5)]-acetic acid, there are recovered, after vacuum distillation of the residue obtained, 10 g of 2-methyl-β-[2-ethyl-indanyl-(5)]-ethanol in the form of a colourless oil.

Boiling point$_{1\ mm\ Hg}=130°$–$132°$ C.

EXAMPLE 35

β-[2-Methyl-indanyl-(5)]-ethanol

Formula I
$R_1=H$
$R_2=CH_3$
$R_3=H$

Following the procedure of Example 33 but using 3.5 g of [2-methyl-indanyl-(5)]-acetic acid, there are recovered, after vacuum distillation of the residue obtained, 2.6 g of β-[2-methyl-indanyl-(5)]-ethanol in the form of a colourless oil.

Boiling point$_{0.5\ mm\ Hg}=115°$ C.

EXAMPLE 36

[2-Isopropyl-indanyl-(5)]-acetic acid (a) [2-Isopropyl-indanyl-(5)]-acetic acid morpholinethioamide

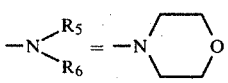

Formula XI
$R_1=H$
$R_2=$isopropyl

A mixture of 100 g of [2-isopropyl-indanyl-(5)]-methyl ketone, 2.2 g of sulphur and 75 g of morpholine is heated at 140° C. for 12 hours. Thereafter, the reaction mixture is concentrated in vacuo and is then taken up in 200 ml of 95° strength ethanol. The crystals formed are filtered off and washed with a small amount of cold 95° strength ethanol. 95 g of [2-isopropyl-indanyl-(5)]-acetic acid morpholinethioamide are thus obtained in the form of light yellow crystals.

Melting point 120° C.

(b) [2-Isopropyl-indanyl-(5)]-acetic acid

Formula I
$R_1=R_3=R_4=H$
$R_2=$isopropyl

A solution of 95 g of [2-isopropyl-indanyl-(5)]-acetic acid morpholinethioaide in 125 ml of acetic acid and 175 ml of hydrochloride acid (d=1.18) is heated under reflux for 18 hours.

The reaction mixture is then poured onto ice and the organic products are extracted with ether. After the ether has been washed carefully with water and dried over sodium sulphate, it is evaporated in vacuo. After recrystallisation of the residue obtained from petroleum ether, 63 g of [2-isopropyl-indanyl-(5)]-acetic acid are isolated in the form of white crystals.

Melting point 80°-81° C.

EXAMPLE 37

β-[2-Isopropyl-indanyl-(5)]-ethanol

Formula I
$R_1=H$
$R_2=$isopropyl
$R_3=H$

Following the procedure of Example 33 but using 25 g of [2-isopropyl-indanyl-(5)]-acetic acid, 20.5 g of β-[2-isopropyl-indanyl-(5)]-ethanol are obtained in the form of white crystals, after recrystallisation from pentane.

Melting point 41°-42° C.

The pharmacological properties of the products of the invention are illustrated by the following experimental results.

Anti-inflammatory activity

The products to be tested are administered orally to batches of 12 SPF male rats, OFA strain, weighing 120–130 g, 2 hours and 30 minutes (½ dose each time) before the subcutaneous plantar injection of 0.05 ml of a 1% strength solution of carraghenine. The volume of the back paw which received the phlogogenic agent is measured at regular intervals. The 50% effective dose is calculated at the moment of greatest swelling of the controls.

The results are given in Tables I to IV below, in which the percentage reduction in the inflammation is noted.

TABLE I

| mg/kg oral administration | Examples 1 and 2 | Example 3 | Example 4 | Example 6 | Example 7 | Example 8 | Example 9 |
|---|---|---|---|---|---|---|---|
| 8 | — | — | — | — | 29 | — | — |
| 16 | — | — | — | — | 43 | — | 47 |
| 32 | — | — | 10 | — | 61 | 17 | 68 |
| 64 | 15 | 24 | 19 | 16 | 73 | 23 | 80 |
| 128 | 42 | 36 | 47 | 39 | 75 | 52 | — |
| 256 | 88 | 56 | 80 | 44 | — | 62 | — |
| $ED_{50}$ mg/kg | 130 | 200 | 120 | >256 | 22 | 150 | 17 |

$ED_{50}$ = 50% effective dose
OA (sic) = oral administration

TABLE II

| mg/kg | Example 11 | Example 12 | Example 13 | Example 14 | Example 15 | Example 16 | Example 17 | Example 18 | Example 19 | Example 20 |
|---|---|---|---|---|---|---|---|---|---|---|
| 4 | — | — | — | — | — | — | — | — | 25 | — |
| 8 | — | — | — | — | — | — | — | — | 20 | — |
| 16 | — | 15 | 23 | 11 | 11 | 4 | 13 | 31 | 44 | 16 |
| 32 | 4 | 23 | 29 | 5 | 20 | 20 | 24 | 54 | 48 | 24 |
| 64 | 8 | 49 | 37 | 16 | 27 | 37 | 30 | 61 | 63 | 25 |
| 128 | 13 | 71 | 47 | 17 | 41 | 61 | 38 | 66 | 67 | 38 |
| 256 | 13 | 80 | 51 | 31 | 68 | 94 | 43 | 77 | 82 | 37 |
| 512 | 32 | — | — | 34 | 72 | — | — | — | — | — |
| $ED_{50}$ mg/kg OA | >512 | 70 | 200 | >512 | 160 | 73 | >256 | 36 | 30 | >256 |

$ED_{50}$ = 50% effective dose
OA = oral administration

TABLE III

| mg/kg | Example 21 | Example 22 | Example 23 | Example 24 | Example 25 | Example 26 | Example 27 | Example 28 | Example 29 | Example 30 | Example 32 |
|---|---|---|---|---|---|---|---|---|---|---|---|
| 4 | — | — | — | — | — | — | 29 | 37 | 12 | 10 | 19 |
| 8 | — | — | — | — | — | — | — | — | — | — | — |
| 16 | — | 17 | — | 7 | 26 | 38 | 54 | 31 | 35 | 32 | 21 |
| 32 | 17 | 7 | 9 | 21 | 28 | 47 | — | — | — | — | — |
| 64 | 25 | 12 | 30 | 36 | 7 | 54 | 61 | 66 | 45 | 55 | 59 |
| 128 | 52 | 11 | 50 | 50 | 12 | 68 | 64 | 72 | 72 | 47 | 55 |
| 256 | 68 | 34 | 55 | 57 | 10 | 70 | 76 | 79 | 65 | 52 | — |
| 512 | — | 52 | 90 | 73 | — | — | — | — | — | — | — |
| $ED_{50}$ mg/kg OA | 130 | 480 | 140 | 142 | >256 | 40 | 22 | 24 | 55 | — | 65 |

$ED_{50}$ = 50% effective dose
OA = oral administration

TABLE IV

| mg/kg oral administration | Example 33 | Example 34 | Example 35 | Example 37 |
|---|---|---|---|---|
| 8 | 0 | — | — | — |
| 16 | 13 | 46 | 43 | 0 |
| 32 | 34 | 42 | 42 | 1 |
| 64 | 52 | 51 | 56 | 21 |
| 128 | 58 | 60 | 76 | 41 |

TABLE IV-continued

| mg/kg oral administration | Example 33 | Example 34 | Example 35 | Example 37 |
|---|---|---|---|---|
| 256 | 63 | 61 | 89 | 30 |
| ED$_{50}$ mg/kg oral administration | 85 | 50 | 35 | >256 |

OA = oral administration
ED$_{50}$ = 50% effective dose

Analgesic activity

The products tested are administered orally to batches of 6 male mice (SPF$_1$, OF$_1$ strain) weighing 19–20 g.

1 hour later, 0.3 ml of a 0.02% strength solution of phenylbenzoquinone is injected intraperitoneally into each mouse and, from the 5th to the 10th minute after the latter treatment, the number of pain reactions (abdominal twistings) is counted.

Table V to VIII below give the percentage inhibition of these reactions.

TABLE V

| mg/kg oral administration | Examples 1 and 2 | Example 3 | Example 4 | Example 5 | Example 6 | Example 7 | Example 8 | Example 9 |
|---|---|---|---|---|---|---|---|---|
| 8 | — | — | — | — | — | 17 | — | — |
| 16 | 25 | 33 | 6 | — | 28 | 61 | — | — |
| 32 | 28 | 51 | 33 | — | 41 | 96 | 10 | 28 |
| 64 | 67 | 66 | 70 | 32 | 59 | — | 67 | 26 |
| 128 | 89 | 66 | 99 | — | 78 | — | 73 | 79 |
| 256 | 94 | 94 | — | 58 | 72 | — | 90 | 97 |
| ED$_{50}$ mg/kg OA | 43 | 33 | 40 | ≈150 | 40 | 14 | 70 | 78 |

ED$_{50}$ = 50% effective dose
OA = oral administration

TABLE VI

| mg/kg CA | Example 11 | Example 12 | Example 13 | Example 14 | Example 15 | Example 16 | Example 17 | Example 18 | Example 19 | Example 20 |
|---|---|---|---|---|---|---|---|---|---|---|
| 2 | — | — | — | — | — | — | — | 18 | — | — |
| 4 | — | — | — | — | — | — | — | 27 | 5 | — |
| 8 | — | — | — | — | 14 | 13 | — | 58 | 31 | — |
| 16 | — | — | 15 | — | 18 | 30 | — | 75 | 54 | — |
| 32 | 15 | 9 | 30 | 20 | 68 | 77 | — | 95 | 82 | 26 |
| 64 | 29 | 20 | 71 | 35 | 91 | 96 | 28 | — | 96 | — |
| 128 | 58 | 46 | 83 | 52 | — | — | 70 | — | — | 27 |
| 256 | 59 | 67 | — | 62 | — | — | 83 | — | — | 74 |
| 512 | 83 | 75 | — | 93 | — | — | 100 | — | — | 100 |
| ED$_{50}$ mg/kg | 140 | 175 | 46 | 110 | 23 | 19 | 100 | 6.5 | 14 | 175 |

ED$_{50}$ = 50% effective dose
OA = oral administration

TABLE VII

| mg/kg OA | Example 21 | Example 22 | Example 23 | Example 24 | Example 25 | Example 26 | Example 27 | Example 28 | Example 29 | Example 30 | Example 32 |
|---|---|---|---|---|---|---|---|---|---|---|---|
| 4 | — | — | — | — | — | — | — | 21 | — | — | — |
| 8 | — | — | 1 | 0 | — | 17 | 7 | 20 | — | — | 6 |
| 16 | — | 13 | 20 | 24 | — | 52 | 42 | 40 | 8 | 11 | 47 |
| 32 | — | 19 | 36 | 32 | 19 | 69 | 69 | 66 | 43 | 32 | 79 |
| 64 | 2 | 73 | 82 | 53 | 50 | 94 | 94 | 86 | 57 | 73 | 99 |
| 128 | 51 | 86 | 45 | 97 | 64 | — | 99 | — | 86 | 99 | — |
| 256 | 71 | 98 | 45 | — | — | — | — | — | 96 | — | — |
| 512 | 81 | — | — | — | — | — | — | — | — | — | — |
| ED$_{50}$ mg/kg | 200 | 45 | >256 | 35 | 80 | 18 | 23 | 20 | 50 | 37 | 18 |

ED$_{50}$ = 50% effective dose
OA = oral administration

TABLE VIII

| mg/kg OA | Example 33 | Example 34 | Example 35 | Example 37 |
|---|---|---|---|---|
| 2 | 6 | — | — | — |
| 4 | 25 | — | — | — |
| 8 | 42 | — | — | — |
| 16 | 68 | — | — | 0 |
| 32 | 90 | 12 | 10 | 40 |
| 64 | — | 22 | 27 | 55 |
| 128 | — | 60 | 69 | 62 |
| 256 | — | 94 | 95 | 81 |
| ED$_{50}$ mg/kg OA | 9 | 95 | 87 | 60 |

ED$_{50}$ : 50% effective dose
OA : oral administration

I claim:

1. A compound selected from the group consisting of the dimethylaminoethyl ester of 2-methyl-[2-isopropyl-indanyl-(5)]-acetic acid, the diethylaminoethyl ester of 2-methyl-[2-isopropyl-indanyl-(5)]-acetic acid and the dimethylamino-α-dimethyl-ethyl ester of 2-methyl-[2-isopropyl-indanyl-(5)]-acetic acid or a pharmaceutically acceptable acid addition salt of said compound.

2. The compound of claim 1 which is the oxalate of the diethylaminoethyl ester of 2-methyl-[2-isopropyl-indanyl-(5)]-acetic acid.

3. The compound of claim 1 which is the maleate of the dimethylamino-α-dimethyl-ethyl ester of 2-methyl-[2-isopropyl-indanyl-(5)]-acetic acid.

4. The compound according to claim 1 which is the hydrochloride of the dimethylaminoethyl ester of 2-methyl-[2-isopropyl-indanyl-(5)]-acetic acid.

* * * * *